(12) United States Patent
Koenig et al.

(10) Patent No.: US 6,689,369 B2
(45) Date of Patent: Feb. 10, 2004

(54) IMMUNOGENIC PNEUMOCOCCAL PROTEIN AND VACCINE COMPOSITIONS THEREOF

(75) Inventors: Scott Koenig, Rockville, MD (US); Leslie S. Johnson, Germantown, MD (US); John E. Adamou, Germantown, MD (US)

(73) Assignee: MedImmune, Inc., Gaithersburg, MD (US)

( * ) Notice: Subject to any disclaimer, the term of this patent is extended or adjusted under 35 U.S.C. 154(b) by 265 days.

(21) Appl. No.: 09/844,124

(22) Filed: Apr. 27, 2001

(65) Prior Publication Data

US 2003/0166844 A1 Sep. 4, 2003

Related U.S. Application Data

(60) Provisional application No. 60/200,074, filed on Apr. 27, 2000.

(51) Int. Cl.[7] ................................................ A61K 39/09
(52) U.S. Cl. ............................... 424/244.1; 424/184.1; 424/185.1; 424/190.1; 530/350
(58) Field of Search .......................... 424/184.1, 185.1, 424/190.1, 244.1; 530/350

(56) References Cited

FOREIGN PATENT DOCUMENTS

| WO | WO9806734 | * | 2/1998 |
|---|---|---|---|
| WO | WO 98/18931 | | 5/1998 |

* cited by examiner

*Primary Examiner*—Jennifer E. Graser
(74) *Attorney, Agent, or Firm*—Elliot M. Olstein; Alan J. Grant (57) ABSTRACT

The present invention relates to novel immunogenic polypeptides, and therapeutically active fragments thereof, and vaccines, and vaccine compositions, for the prevention and treatment of streptococcal infection, especially by *Streptococcus pneumoniae*. The invention also relates to antibodies against the disclosed polypeptides, as well as methods of disease prevention and/or treatment.

19 Claims, 4 Drawing Sheets

Strain SJ2 (serotype 6B)

IMMUNOGENIC PNEUMOCOCCAL PROTEIN AND VACCINE COMPOSITIONS THEREOF

This application claims the priority of U.S. Provisional Application No. 60/200,074, filed Apr. 27, 2000, the disclosure of which is hereby incorporated by reference in its entirety.

FIELD OF THE INVENTION

This invention relates to the field of bacterial surface proteins and their use as components in vaccines and vaccine compositions for protection against bacterial infections.

BACKGROUND OF THE INVENTION

*Streptococcus pneumoniae* (*S. pneumoniae*; pneumococcus) is a gram positive bacterium that is also a major causative agent of invasive infections in animals and humans, including such diseases as sepsis, menningitis, otitis media, and lobar pneumonia. (Tuomanen et al, *New Engl. J. Med.*, 322:1280–1284 (1995)) As part of the infective process, pneumococci readily bind to non-inflamed human epithelial cells of the upper and lower respiratory tract by binding to eukaryotic carbohydrates in a lectin-like manner (Cundell et al, *Micro. Path.*, 17:361–374 (1994)). Conversion to invasive pneumococcal infections for bound bacteria may involve the local generation of inflammatory factors that may activate the epithelial cells to change the number and type of receptors on their surfaces. (Cundell et al, *Nature*, 377:435–438 (1995)) It has been suggested that one such receptor, platelet activating factor (PAF), is engaged by the pneumococcal bacteria and, within a short period of time, perhaps as short as minutes later, following appearance of PAF, the pneumococcal organisms exhibit strongly enhanced adherence to, and invasion of, tissue. Certain soluble receptor analogs have been shown to prevent the progression of pneumococcal infections (Idanpaan-Heikkila et al, *J. Inf. Dis.*, 176:704–712 (1997)). Other proteins have been suggested as being involved in the pathogenicity of *S. pneumoniae*, but the majority of the gene products have not been characterized.

Thus, although it would be highly advantageous to have characterized samples of polypeptides having epitopes in common from various strains of *S. pneumoniae* for use as vaccines and as components in vaccine compositions to provide protection against a wide variety of *S. pneumoniae* serotypes, the lack of purified and/or characterized polypeptides from such sources has represented a severe drawback to such testing and evaluation. The present invention solves this problem by providing a recombinant polypeptide derived from pneumococcus with demonstrated protective ability.

BRIEF SUMMARY OF THE INVENTION

It is an object of the present invention to provide isolated and/or purified polypeptide material for use in forming therapeutically effective vaccines and vaccine compositions as well as polynucleotides encoding them.

It is also an object of the present invention to provide vaccines and vaccine compositions with therapeutic activity in the prevention and/or treatment of bacterially caused diseases, especially those caused by one or more strains of *S. pneumoniae*.

It is another object of the present invention to provide antibodies, either polyclonal or monoclonal, specific for the polypeptides of the present invention which can serve in both diagnostic and therapeutic uses.

It is a further object of the present invention to provide processes for the prevention and treatment of diseases caused by pneumococcal organisms wherein said prevention and/or treatment relies on the use of vaccines, or vaccine compositions, comprising polypeptides as disclosed herein. Such prevention and/or treatment may also rely on compositions comprising antibodies specific for the polypeptides of the present invention.

It is a still further object of the present invention to provide processes for the recombinant production of novel pneumococcal polypeptides, for the production of vaccines incorporating such polypeptides, including prophylactically and therapeutically active fragments thereof, as well as the production of antibodies specific for epitopes found on such polypeptides. Such processes may include the production of recombinant vectors and cells comprising polynucleotides encoding the polypeptides disclosed herein.

BRIEF DESCRIPTION OF THE DRAWINGS

FIG. 1 shows the results of experiments (FIGS. 1A and 1B, respectively) using the preparations of recombinant SP133 polypeptide of the invention. The experimental data show that active immunization with recombinant SP133 polypeptide derived from pneumococcal strain Norway 4 serotype (N4) protected mice from death in a model of pneumococcal sepsis using a heterologous strain SJ2 (serotype 6B)). In the experiment shown in FIG. 1A, four of ten mice immunized with SP 133 survived the 15-day observation period following challenge with approximately 800 CFU (colony forming units) of pneumococci. Conversely, all ten of the sham immunized mice (injected only with phosphate buffered saline (PBS) plus adjuvant) died by day 12. The experiment shown in FIG. 1B employed 20 mice immunized with recombinant SP133. The results show that nine of these mice survived the 15 day observation period following challenge with about 340 CFU of pneumococci. Conversely, seventeen of nineteen of the sham immunized mice DIED during the same period. In both experiments, mice immunized with recombinant SP133 polypeptide showed a significant difference in the number of survivors compared to that of the sham immunized mice (P<0.05).

FIG. 4 is a western blot showing the reactivity of patient sera with SP133. The recombinant SP133 protein was separated by SDS-PAGE and transferred onto nitrocellulose. Sera were collected from 4 patients (indicated by the numeral at the top) at two different times. The first collection (denoted "A" for acute serum) was soon after onset of illness while the second collection (denoted "C" for "convalescent serum") was made eight to thirty days later. These sera were used to probe the blots. The data show that for patients 1 and 2, convalescent serum reacted more strongly with SP133 than did the corresponding acute serum.

DETAILED SUMMARY OF THE INVENTION

The present invention relates generally to the field of bacterial antigens and their use, for example, as immunogenic agents in humans and animals to stimulate an immune response. More specifically, it relates to the vaccination of mammalian species with a polypeptide obtained from *Streptococcus pneumoniae* species as a mechanism for stimulating production of antibodies that protect the vaccine recipient against infection by a wide range of serotypes of pathogenic *S. pneumoniae*.

The present invention further relates to antibodies against such polypeptides, which antibodies (whether polyclonal or monoclonal) find use in diagnosis and/or passive immune therapy of such pneumococcal infections.

In a specific embodiment, the present invention relates to the prevention and/or treatment of pneumococcal infections such as infections of the middle ear, nasopharynx, lung and bronchial areas, blood, cerebrospinal fluid, and others, that are caused by pneumococcal bacteria.

In accordance with the foregoing, the present invention relates to a purified polypeptide comprising an amino acid sequence shown in SEQ ID NO: 4. The present invention, however, is broad enough also to encompass polypeptides having at least about 80% identity to the amino acid sequence of SEQ ID NO: 4, preferably at least about 90% sequence identity, or homology, therewith, most preferably at least about 95% identity to the amino acid sequence of SEQ ID NO: 4, especially at least about 98% identity to the amino acid sequence of SEQ ID NO: 4, with a polypeptide having the amino acid sequence of SEQ ID NO: 4 being a preferred embodiment.

In accordance with the present invention, the term "percent identity" or "percent identical," including percent (%) homology, when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100[1−(C/R)]

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

The present invention further relates to a polypeptide which has the deduced amino acid sequence (SEQ ID NO:4), as well as fragments, analogs and derivatives of such polypeptide.

The terms "fragment," "derivative" and "analog" when referring to the polypeptide (SEQ ID NO:4), means a polypeptide which retains essentially the same biological function or activity as such polypeptide. Thus, an analog includes a proprotein which can be activated by cleavage of the proprotein portion to produce an active mature polypeptide. Such fragments, derivatives and analogs must have sufficient similarity to the polypeptide of SEQ ID NO:4 so that activity of the native polypeptide is retained.

The polypeptide of the present invention may be a recombinant polypeptide, a natural polypeptide or a synthetic polypeptide, preferably a recombinant polypeptide.

The fragment, derivative or analog of the polypeptide (SEQ ID NO:4) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

In separate embodiments, the present invention relates to an isolated polypeptide comprising an amino acid sequence at least about 80% identical to the amino acid sequence of SEQ ID NO: 4, preferably at least about 90% identical to the amino acid sequence of SEQ ID NO: 4, most preferably at least about 95% identical to the amino acid sequence of SEQ ID NO: 4, especially where said isolated polypeptide has a sequence at least about 98% identical to the amino acid sequence of SEQ ID NO: 4, and most especially where said isolated polypeptide comprises a polypeptide having the amino acid sequence of SEQ ID NO: 4, including all immunogenically active fragments of any of the aforementioned isolated polypeptides.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention further relates to an isolated and/or purified polynucleotide comprising the nucleotide sequence of SEQ ID NO: 3 as well as a polynucleotide having the nucleotide sequence of SEQ ID NO: 3. However, the polynucleotides of the present invention are defined sufficiently broadly to also encompass a nucleotide sequence at least 65% identical to a polynucleotide sequence encoding the polypeptide of SEQ ID NO 4, preferably a polynucleotide having a nucleotide sequence at least 80% identical to a nucleotide sequence encoding the polypeptide of SEQ ID NO:4, most preferably a polynucleotide having a nucleotide sequence at least 95% identical to a nucleotide sequence encoding the polypeptide of SEQ ID NO:4, especially where the polynucleotide has a nucleotide sequence at least about 98% identical to a nucleotide sequence encoding the amino acid sequence of SEQ ID NO:4, with a polynucleotide encoding the polypeptide of SEQ ID NO: 4 being especially preferred. Thus, a polynucleotide comprising the nucleotide sequence of SEQ ID NO: 3 is most especially preferred.

As used herein and except as noted otherwise, all terms are defined as given below.

In accordance with the present invention, the term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

"Isolated" in the context of the present invention with respect to polypeptides (or polynucleotides) means that the material is removed from its original environment (e.g., the natural environment if it is naturally occurring). For example, a naturally-occurring polynucleotide or polypeptide present in a living organism is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment. The polypeptides and polynucleotides of the present invention are preferably provided in an isolated form, and preferably are purified to homogeneity.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 0.001%, or at least 0.01% or 0.1%; and even desirably 1% by weight or greater is expressly contemplated.

The term "coding region" refers to that portion of a gene which either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

In accordance with the present invention, the term "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

In forming the DNA constructs for coding for the polypeptides according to the present invention, the forward and reverse primers for polymerase chain reaction synthesis are given as SEQ ID NOS.: 1 and 2, respectively.

The term "expression product" means that polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region whose expression product retains essentially the same biological function or activity as the expression product of the complete coding region.

The term "primer" means a short nucleic acid sequence that is paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "open reading frame (ORF)" means a series of triplets coding for amino acids without any termination codons and is a sequence (potentially) translatable into protein.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to a polynucleotides, such terms refer to the products produced by treatment of said polynucleotides with any of the common endonucleases.

In applying the techniques utilized in accordance with the present invention, many conventional molecular biological procedures and protocols are to be found in the literature and are well known to those skilled in the art. Among the more useful reference sources are the following: Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols*, in *Methods in Molecular Biology*, Vol. 62, (Tuan, ed., Humana Press, Totowa, N.J., 1997), the disclosures of which are hereby incorporated by reference.

The present invention also relates to a vaccine, or a vaccine composition, comprising a polypeptide, including immunogenic fragments thereof, selected from the polypeptides, and immunogenic fragments thereof, disclosed according to the present invention and wherein said polypeptides and fragments are in a pharmaceutically acceptable carrier and wherein said polypeptide and/or fragments are present in an amount effective to elicit antibodies, preferably protective antibodies, in an animal against an organism of the genus Streptococcus.

The vaccine compositions of the present invention may, as stated, comprise immunogenically active fragments of the polypeptides disclosed herein, such as the polypeptide of SEQ ID NO: 4, and, where this is the case, such fragments will commonly be of varying sizes but will commonly be immunogenic fragments at least about 200 amino acid residues in length, plus or minus 5 residues, preferably at least about 250 amino acid residues in length, and most preferably at least 270 amino acid residues in length, plus or minus about 5 residues.

The vaccine compositions of the present invention may also comprise polynucleotides as disclosed herein.

Generally, vaccines are prepared as injectables, in the form of aqueous solutions or suspensions. Vaccines in an oil base are also well known such as for inhaling. Solid forms which are dissolved or suspended prior to use may also be formulated. Pharmaceutically acceptable carriers, diluents and excipients are generally added that are compatible with the active ingredients and acceptable for pharmaceutical use.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON's PHARMACEUTICAL SCIENCES (Mack Pub. Co., N.J. current edition).

Vaccine compositions may further incorporate additional substances to stabilize pH, or to function as adjuvants, wetting agents, or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art, or for administration through nasal or respiratory routes.

The amount of vaccine sufficient to confer immunity to pathogenic bacteria, viruses, or other microbes is determined by methods well known to those skilled in the art. This quantity will be determined based upon the characteristics of the vaccine recipient and the level of immunity required. Typically, the amount of vaccine to be administered will be determined based upon the judgment of a skilled physician. Where vaccines are administered by subcutaneous or intramuscular injection, a range of 0.5 to 500 $\mu$g purified protein may be given. As useful in the present invention, such dosages are commonly sufficient to provide about 1 $\mu$g, possibly 10 $\mu$g, even 50 $\mu$g, and as much as 100 $\mu$g, up to 500 $\mu$g of immunogenic protein, or immunogenic polypeptide, or immunogenically active fragments thereof. In addition, more than one such active material may be present in the vaccine. Thus, more than one antigenic structure may be used in formulating the vaccine, or vaccine composition to use in the methods disclosed herein. This may include two or more individually immunogenic proteins or polypeptides, proteins or polypeptides showing immunogenic activity only when in combination, either quantitatively equal in their respective concentrations or formulated to be present in some ratio, either definite or indefinite. Thus, a vaccine composition for use in the processes disclosed herein may include one or more immunogenic proteins, one or more immunogenic polypeptides, and/or one or more immunogenically active immunogens comprising antigenic fragments of said immunogenic proteins and polypeptides, the latter fragments being present in any proportions selected by the use of the present invention. The exact components, and their respective quantities, making up the vaccines, and vaccine compositions, useful in the methods of the present invention are determined, inter alia, by the nature of the disease to be treated or prevented, the severity of such condition where it already exists, the age, sex, and general health of the recipient, as well the personal and professional experience and inclinations of the researcher and/or clinician utilizing these methods.

The present invention also contemplates use of a vaccine composition comprising a polynucleotide encoding a polypeptide, including immunogenic fragments thereof, selected from any of the polypeptides disclosed according to the invention and wherein said polynucleotide is suspended in a pharmaceutically acceptable carrier and wherein said polynucleotide is present in an amount effective to elicit protective antibodies in an animal against an organism of the genus Streptococcus.

The present invention further relates to an isolated antibody that binds specifically to a polypeptide selected from the group consisting of the polypeptides, and immunogenic fragments thereof, disclosed herein. Such an isolated antibody may be either a polyclonal or a monoclonal antibody.

Still another aspect of the present invention relates to a method of using one or more antibodies (monoclonal or polyclonal, natural or recombinant, and regardless of how prepared, i.e., by purification from a natural source, or generated by cloning or by direct chemical synthesis), preferably, but not necessarily, specific for one or more antigenic determinants present in the vaccine, or vaccine composition selected for use in the methods of the present invention.

Thus, the present invention also relates to a composition comprising one or more of the isolated antibodies disclosed herein wherein said antibody is suspended in a pharmaceutically acceptable carrier, including all suitable and equivalent diluents or excipients as described hereinabove and wherein said antibody is present in said composition in a therapeutically effective amount so as to protect an animal against an organism of the genus Streptococcus.

The present invention further relates to methods of using the vaccine compositions and antibody compositions disclosed herein in prophylactically and therapeutically effective manner to present and/or treat disease. Thus, the present invention is also directed to a method of preventing or attenuating an infection caused by a member of the genus Streptococcus in an animal, most preferably where said animal is a human patient, infected therewith, or at risk of infection therewith, comprising administering to said animal a therapeutically effective amount of a vaccine composition as disclosed herein according to the present invention.

The present invention further relates to a method of preventing or attenuating an infection caused by a member of the genus Streptococcus in an animal infected therewith, or at risk of infection therewith, comprising administering to said animal, most preferably where said animal is a human patient, a therapeutically effective amount of the one or more of the antibodies disclosed herein according to the present invention, wherein said antibody is administered in an amount effective to prevent or attenuate said infection.

The vaccine compositions of the present invention that are useful for treating disease, especially pneumococcal disease, are not limited to those containing purified, or isolated, polypeptides, and immunogenically active fragments thereof, as disclosed herein but also include compositions formed of microorganisms wherein the microorganism expresses and presents the immunogenic polypeptide, or fragment thereof, to the immune system. Such microorganisms, to find use in the methods of the present invention, may be suitably attenuated so as to avoid other complications, or possible superinfection.

Thus, the present invention includes a vaccine composition comprising a microbial organism transformed with polynucleotides, and thereby expressing the polypeptides, or immunogenic fragments thereof, selected from the group consisting of the polypeptides disclosed herein, such as the polypeptide, and homologous polypeptides thereof, of SEQ ID NO: 4.

In utilizing such vaccine compositions, the microorganisms finding most use for the methods of the present invention include, but are not necessarily limited to, the group consisting of Salmonella, Mycobacteria, Streptococcus, poxviruses, and adenoviruses.

The present invention also relates to vectors comprising the polynucleotides disclosed herein.

The present invention further relates to recombinant cells comprising within their genomes, or within vectors or other extrachromasomal polynucleotides incorporated into said cells, wherein said polynucleotides have sequences selected from the sequences disclosed herein. Such cells find use as a means of expressing, and secreting, the polypeptides of the present invention and include mammalian cells genetically engineered to produce such polypeptides, the latter commonly being encoded by polynucleotides of the invention present within such recombinant cells. For such purposes, the term "expressing" may or may not include secretion of said protein. Thus, if a recombinant cell synthesizes the polypeptide only internally, which polypeptide must then be collected by lysing the cells and isolating the polypeptide from the lysate, this process would be encompassed by the term "expressing" or "expression."

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* Trp1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use, such as where the SP133 protein is to be expressed from such cells or where such cells are to be used as components of a vaccine composition, are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

EXAMPLE 1

Active Protection with Anti-SP133

A. Cloning, Expression and Purification of SP133

The genomic DNA used as the target for amplification was isolated from *Streptococcus pneumoniae* (strain N4), the same strain used for genomic sequencing. The nucleotide sequence of the gene fragment encoding SP133 is contained in SEQ ID NO:3 and the corresponding amino acid sequence for polypeptide SP133 in SEQ ID NO: 4. Primers (SEQ ID NOS: 1 and 2) were designed so as to amplify the SP133 gene fragment and facilitate cloning thereof into the expression vector pQE10 with, for example, subsequent expression of a histidine-tagged protein product for purification by Nickel-affinity chromatography. Cloning of the fragment amplified by the primers of SEQ ID NOs: 1 and 2 eventually results in the polypeptide of SEQ ID NO: 4 (which is denoted SP133). Of course, this protein may also readily be synthesized directly by chemical means using SEQ ID NO: 4.

B. Vaccination with SP133 Results in Protection Against Lethal *S. pneumoniae* Challenge In each of the experiments shown in FIGS. 1A and 1B, C3H/HeJ mice were immunized subcutaneously (s.c.) with SP133 protein (15 µg in 50 µl PBS emulsified in 50 µl complete Freund's adjuvant [CFA]). Groups of 10 or 19 sham-immunized mice received PBS (phosphate buffered saline) with adjuvant only. A second immunization of 15 µg protein with incomplete Freund's adjuvant (IFA) was administered 3 weeks later. The sham groups received PBS with IFA. Blood was drawn (by retro-orbital bleed) at week 7. Sera from each group were pooled for analysis of anti-SP133 antibody by ELISA. Mice were challenged at week 8 by an intraperitoneal (i.p.) injection of approximately 800 colony forming units (CFU) or 340 CFU of *S. pneumoniae* strain SJ2 (serotype 6B; provided by P. Flynn, St. Jude Children's Research Hospital, Memphis, Tenn.). In preliminary experiments, the $LD_{50}$ of this strain was determined to be about 10 CFU. Mice were monitored for 15 days for survival. A two-sample Log-rank test was used to evaluate the protection against death in a mouse model of systemic disease.

Figure 1:
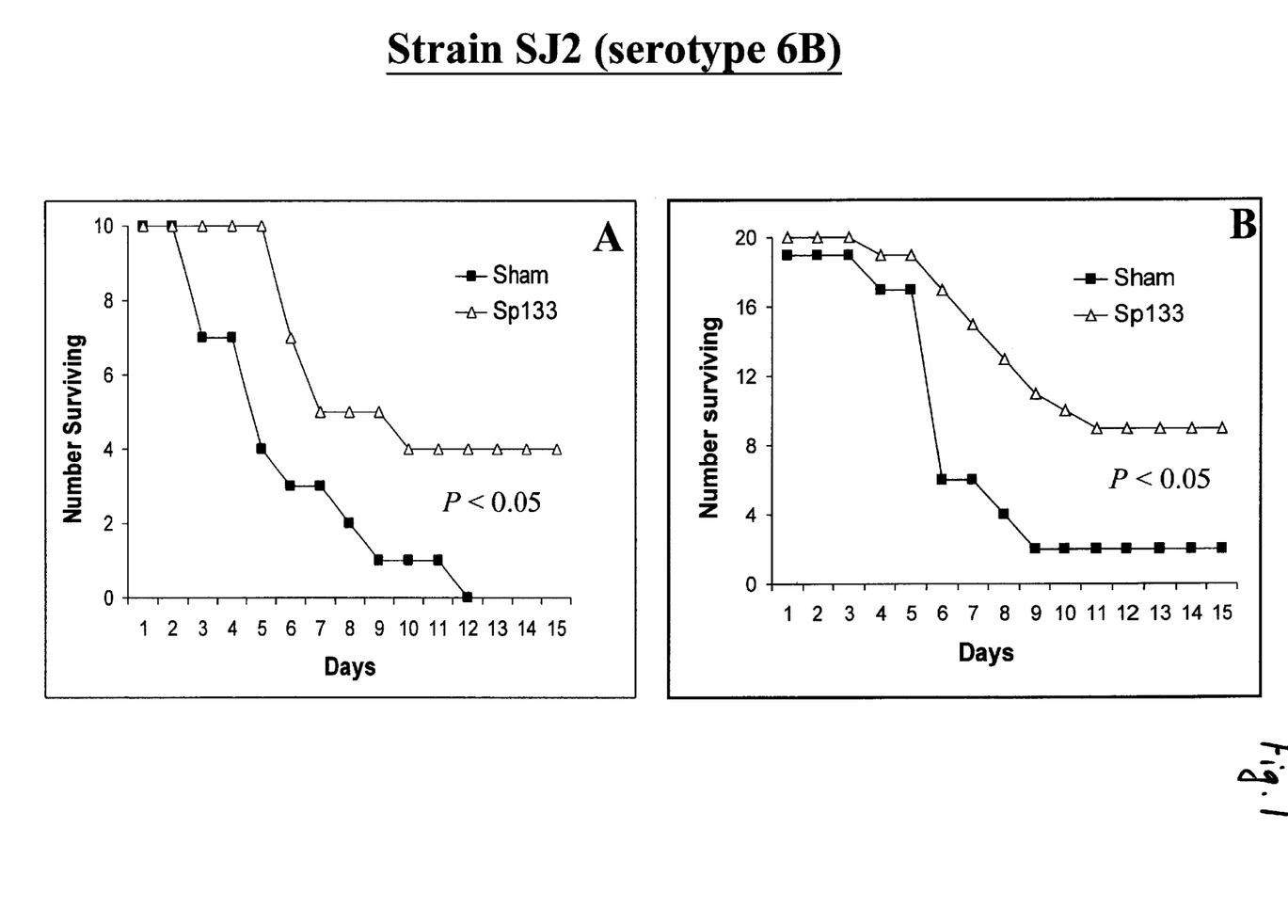

The two experiments shown in FIGS. 1A and 1B used the same preparations of recombinant SP133.

In the experiment shown in FIG. 1A, sera collected 7 weeks following the primary immunization from the ten mice immunized with SP133 had an endpoint ELISA titer of 1:2,048,000. No anti-SP133 antibody was detected in sera from sham-immunized mice. Four of 10 mice immunized with SP133 protein survived the challenge (800 CFU of pneumococci) for the duration of the study (15 days). All 10 of the sham-immunized mice were dead by day 12.

In the experiment shown in FIG. 1B, sera collected 7 weeks following the primary immunization from the 20 mice immunized with SP133 had an endpoint ELISA titer of 1:1,024,000. No anti-SP133 antibody was detected in sera from sham-immunized mice. Nine of twenty mice immunized with SP133 protein survived the challenge (340 CFU of pneumococci) for the duration of the study (15 days). Seventeen of nineteen of the sham-immunized mice were dead by day 9.

These data demonstrate that immunization of mice with recombinant SP133 protein elicited a response capable of protecting mice against systemic pneumococcal infection and death (P<0.05 for both studies). Cross protection was demonstrated by the fact that the recombinant pneumococcal protein was generated based on a serotype 4 (Norway 4 strain) DNA sequence, while the challenge employed a heterologous strain SJ2 (serotype 6B).

EXAMPLE 2

Cell Surface Labeling of *Streptococcus pneumoniae*

A. Flow Cytometric Analysis

Pneumococci (strain SJ2) were cultured in Todd Hewitt broth supplemented with 0.5% yeast extract (THY) medium at 37° C. to mid-logarithmic phase. Bacteria were harvested and washed once in PBS containing 5% heat inactivated fetal calf serum (FCS; BioWhittaker, Walkersville, Md.) at 4,000×g for 10 minutes. Bacterial cell numbers were adjusted to $5 \times 10^6$ bacteria in 0.1 ml/tube. Pooled sera from mice immunized with SP133 (as already described for Example 1) diluted to 1:100 was added to each tube and placed on ice for 1 hr. Excess antibody was washed off by centrifugation in 1 ml of PBS containing FCS (wash buffer). Alexa 488-conjugated goat anti-mouse Ig (Molecular Probes, Eugene, Oreg.) was added at 1 µg per $5 \times 10^6$ bacteria and placed on ice for 30 minutes. After washing, the samples were suspended in wash buffer and analyzed by flow cytometry with a Becton Dickinson FACStar® Plus using Lysys II software for data acquisition and analysis. Increase in mean channel fluorescence was indicative of binding by the primary immune sera. Immune sera against CbpA (see FIG. 2), a known bacterial cell surface protein, was used as a positive control.

Figure 2:
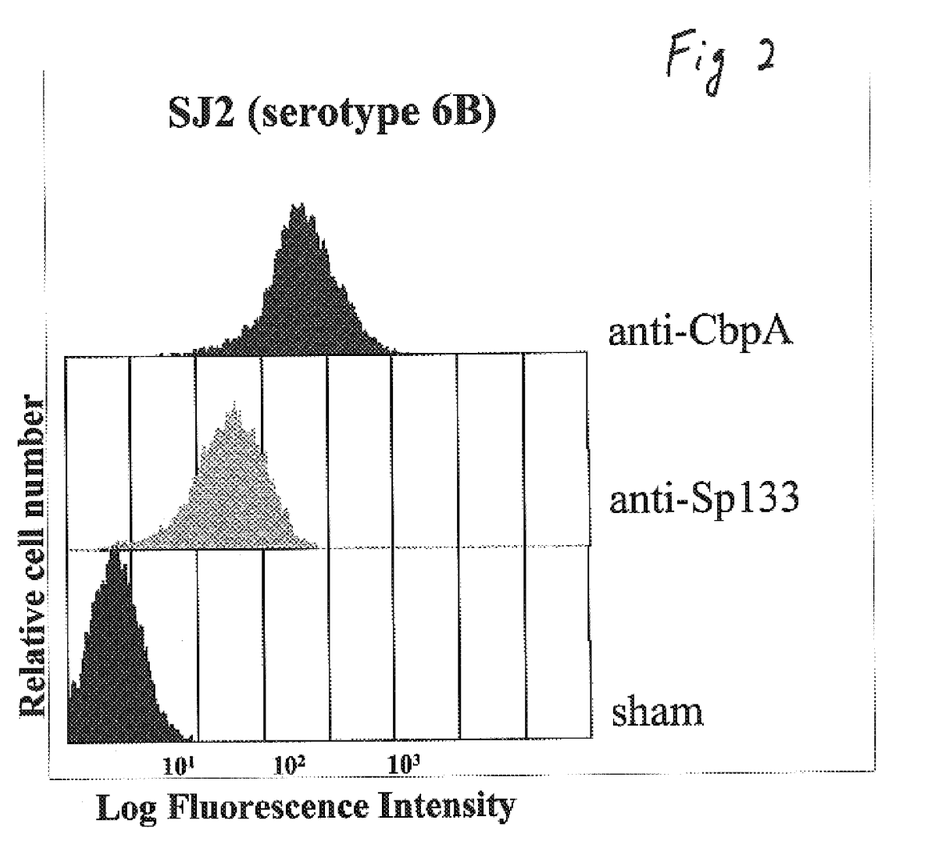
FIG. 2 shows the detection of SP133 on the bacterial cell surface by immunolabeling and flow cytometry. The results demonstrate that immune sera raised against SP133 protein can label the cell surface of intact pneumococci (strain SJ2).

Antisera to SP133 resulted in surface labeling of the SJ2 bacteria as visualized by flow cytometry (FIG. 2). These data show that the native SP133 protein is exposed on the cell surface of intact pneumococci (strain SJ2).

EXAMPLE 3

Conservation of SP133 among strains of *S. pneumoniae*

A. Western Blot Analysis

The pneumococcal strains used in this experiment were obtained from the American Type Culture Collection (10801 University Blvd., Manassas, Va. 20110-2209) and include one isolate from each of the serotypes in the multivalent pneumococcal carbohydrate vaccine. In addition, several laboratory strains and various primary clinical isolates including N4 (Serotype 4) and SJ2 (serotype 6B) were examined for SP133 expression. To prepare total cell lysates, pneumococci were grown to mid-logarithmic phase (absorbance at 620 nm, 0.4 to 0.6) in 2 ml Todd-Hewitt broth with 0.5% yeast extract (Difco, Detroit, Mich.) at 37° C. Bacteria were harvested by centrifugation and washed twice with water. Pellets were resuspended in 200 µl lysis buffer (0.01% sodium dodecyl sulfate, 0.15 M sodium citrate and 0.1% sodium deoxycholate) and incubated at 37° C. for 30 minutes, then diluted in an equal volume 2×SSC (0.3 M sodium chloride, 0.03 M sodium citrate). Proteins in lysates were separated by SDS-PAGE, transferred to nitrocellulose membranes (Bio-Rad Laboratories, Hercules, Calif.) and probed with an antibody in a standard Western blotting procedure. Pooled sera from mice immunized with SP133 (as described in Example 1) was used at a dilution of 1:3,000. Bound antibody was detected with peroxidase-conjugated goat anti-mouse IgG using the chemiluminescence kit from Pharmacia Amersham, Inc. (Piscataway, N.J.).

Figure 3:
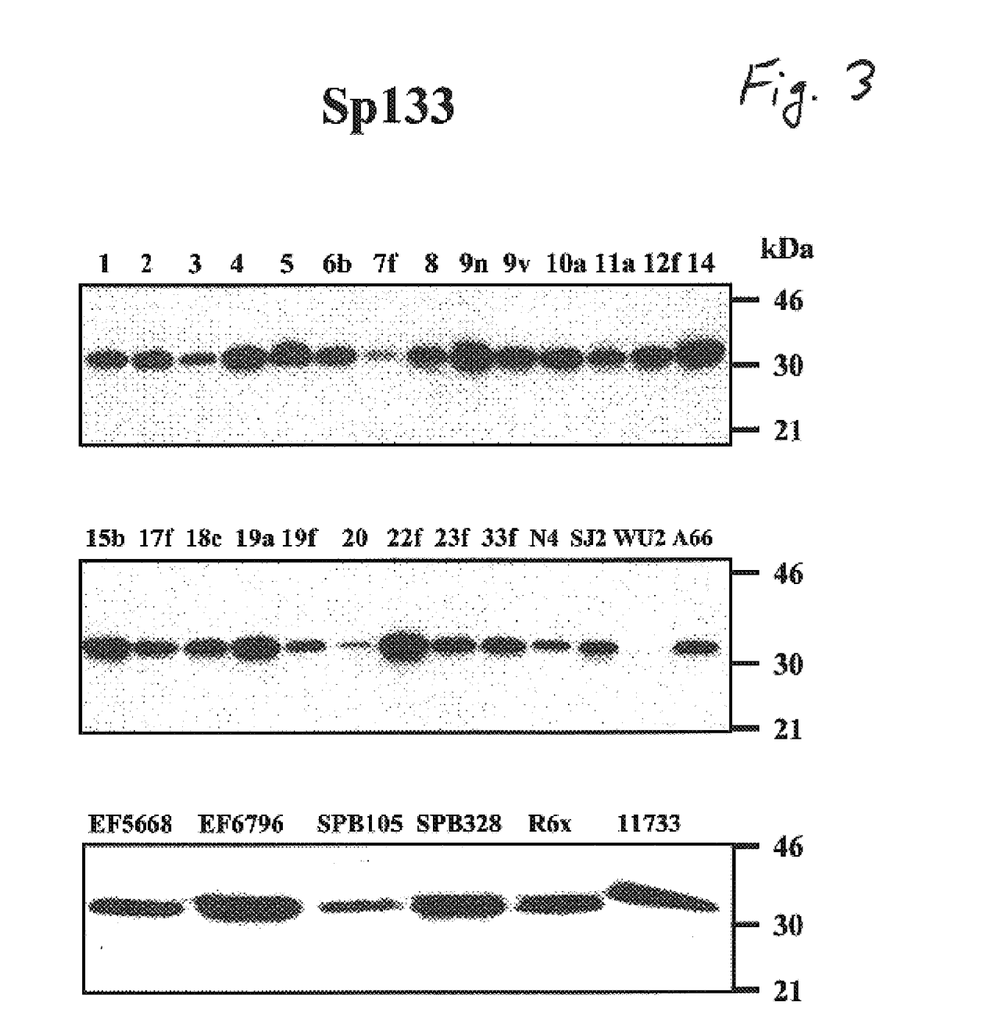
FIG. 3 is a western blot of whole-cell lysates prepared from each of the 23 serotypes included in currently available pneumococcal vaccine probed with antiserum raised against recombinant SP133 polypeptide. Nearly all of the *S. pneumoniae* strains tested detected a protein with molecular mass of approximately 32 kDa (that reacted with the anti-SP133 antiserum), consistent with the predicted molecular mass of SP133. Although SP133 protein was not detected in a lysate prepared from a serotype 3 strain (WU2) SP133 protein was detected in two other serotype 3 strains (ATCC3 and A66).

The mouse anti-SP133 sera detected a major band with an apparent molecular weight of 32 kDa in all pneumococcal lysates tested (except for strain WU2; see FIG. 3).

These data indicate that SP133 is antigenically conserved among strains of the 23 pneumococcal serotypes represented in the currently used polysaccharide vaccine.

EXAMPLE 4

Immunogenicity of SP133 in Humans

Figure 4:
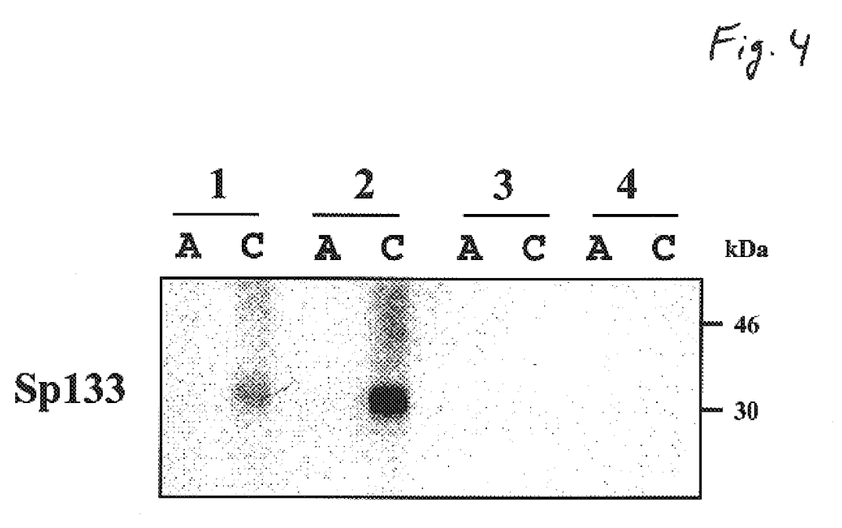

In order to determine whether SP133 is immunogenic during pneumococcal infection in humans, sera from patients with culture-confirmed pneumococcal bacteremia (patients 1, 2, 3, and 4; serotypes 1, 12, 5, and 18C, respectively) were examined in Western blots containing recombinant SP133 protein. In the experiment shown in FIG. 4, sera from four patients (indicated as 1 through 4) were diluted 1:500 and used to probe blots containing SP133 (lacking the signal sequence). Lanes labeled A (acute) were probed with serum collected shortly after diagnosis of pneumococcal infection. Lanes labeled C (convalescent) were probed with serum collected either one month (patients 1 and 2) or eight days after the first serum collection (patients 3 and 4). For patients 1 and 2, reactivity of the convalescent sera with SP133 was stronger than that of the corresponding acute sera.

These data indicate that SP133 is recognized by the human immune system and suggest that antibodies able to bind the SP133 protein may be produced during natural *S. pneumoniae* infection in humans. Since the patients were infected with a variety of pneumococcal strains, these data also support a conclusion that SP133 is antigenically conserved.

What is claimed is:

1. An isolated polypeptide comprising an amino acid sequence at least 90% identical to the amino acid sequence of SEQ ID NO: 4 wherein said polypeptide elicits production of an antibody against *Streptococcus pneumoniae* when administered to mouse.

2. The isolated polypeptide of claim 1 wherein said polypeptide is at least 95% identical to the amino acid sequence of SEQ ID NO: 4.

3. The isolated polypeptide of claim 1 wherein said polypeptide is at least 98% identical to the amino acid sequence of SEQ ID NO: 4.

4. The isolated polypeptide of claim 1 wherein said polypeptide comprises the amino acid sequence of SEQ ID NO: 4.

5. A vaccine composition comprising an immunogenic fragment of the polypeptide of SEQ ID NO:4 wherein said immunogenic fragment is at least 250 contiguous amino acids in length and wherein said immunogenic fragment is in a pharmaceutically acceptable carrier and wherein said immunogenic fragment is present in an amount effective to elicit protective antibodies in an animal against an organism of the genus Streptococcus.

6. The vaccine composition of claim 5 wherein said immunogenic fragments is at least 265 contiguous amino acid residues in length.

7. The vaccine composition of claim 5 wherein said immunogenic fragment is at least 270 contiguous amino acid residues in length.

8. The vaccine composition of claim 5 wherein said immunogenic fragment is at least 275 contiguous amino acid residues in length.

9. An isolated immunogenic fragment of a polypeptide comprising SEQ ID NO: 4 wherein said fragment, when administered to an animal, elicits production of an antibody that binds to the polypeptide having the amino acid sequence SEQ ID NO: 4 and wherein said fragment comprises at least 250 contiguous amino acid residues of SEQ ID NO: 4.

10. The isolated immunogenic fragment of claim 9 wherein said fragment is at least 265 contiguous amino acids in length.

11. The isolated immunogenic fragment of claim 9 wherein said fragment is at least 270 contiguous amino acids in length.

12. The isolated immunogenic fragment of claim 9 wherein said fragment is at least 275 contiguous amino acids in length.

13. A vaccine composition comprising the polypeptide of SEQ ID NO:4 wherein said polypeptide is in a pharmaceutically acceptable carrier and wherein said polypeptide is present in an amount effective to elicit protective an bodies in an animal against an organism of the genus Streptococcus.

14. A method for preventing or treating an infection caused by a member of the genus Streptococcus in an animal comprising administering to said animal a therapeutically effective amount of the vaccine composition of claim 13.

15. The method of claim 14 wherein said animal is a mammal.

16. The method of claim 15 wherein said mammal is a mouse.

17. A method for preventing or treating an infection caused by a member of the genus Streptococcus in an animal comprising administering to said animal a therapeutically effective amount of the vaccine composition of claim 5.

18. The method of claim 17 wherein said animal is a mammal.

19. The method of claim 18 wherein said mammal is a mouse.

* * * * *

SEQUENCE LISTING

```
<160> NUMBER OF SEQ ID NOS: 4

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence:Primer for
      synthesis of Sp133.

<400> SEQUENCE: 1
tcagccatgg gaacagatgt tcaaaaagtt atcgatg                              37

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:Primer
      forsynthesis of Sp133.

<400> SEQUENCE: 2
tgacagatct tccaccgtcc tctagcgcct t                                    31

<210> SEQ ID NO 3
<211> LENGTH: 837
<212> TYPE: DNA
<213> ORGANISM: Artificial Sequence
<220> FEATURE:
```

<223> OTHER INFORMATION: Description of Artificial Sequence:cDNA
       coding for Sp133 protein.

<400> SEQUENCE: 3

| | | | | | |
|---|---|---|---|---|---|
| acagatgttc | aaaaagttat | cgatgaaacc | tatgtccaac | ctgaatatgt | cctaggttcc | 60 |
| tccctatctg | aagaccaaaa | aaatcaaact | cttaaaaaac | tgggctacaa | tgcctcaaca | 120 |
| gataccaaag | aactcaagac | catgacacct | gatgtttatt | ctaaaatcat | gaatgtggcc | 180 |
| aatgactcta | gcttacagtt | gtattcatca | gccaagattc | aaaagctagg | tgacaaatcg | 240 |
| ccacttgagg | tcaagattga | aacaccagaa | aatatcacta | aggtgactca | ggatatgtac | 300 |
| cgaaacgcag | cagtaacgct | gggtatggaa | catgccaaaa | tcactgtagc | agcccctatt | 360 |
| ccagttacag | gagaaagtgc | tttagcaggg | atttactatt | cgctagaggc | taatggagcc | 420 |
| aaggtgccac | aagctaataa | agatttggct | caagaagagc | taaaagcttt | gtcagatatc | 480 |
| aatgctgaaa | acaaggacaa | atcaggctat | gatgctaata | aattaaacgt | tgccctagct | 540 |
| gatatcaagt | caggactcgc | caaagctaaa | gaaagtaagg | gaaatctgac | agaagaagat | 600 |
| atccgcaaga | ttgttgaaga | taccttaaaa | aattacaaac | ttgatcaggt | cataacagga | 660 |
| aaccagatca | atatcatcat | caattttgcc | ttgaatctct | caaagagtga | tatcctcagc | 720 |
| aatgcagatt | tcactaaaac | cctaaatgac | cttaaacaaa | gcatcgtatc | acaagctggc | 780 |
| gacagtttta | aaaatatcaa | ccttaacttt | gatgcggata | aggcgctaga | ggaccct | 837 |

<210> SEQ ID NO 4
<211> LENGTH: 279
<212> TYPE: PRT
<213> ORGANISM: Streptococcus pneumoniae

<400> SEQUENCE: 4

Thr Asp Val Gln Lys Val Ile Asp Glu Thr Tyr Val Gln Pro Glu Tyr
 1               5                  10                  15

Val Leu Gly Ser Ser Leu Ser Glu Asp Gln Lys Asn Gln Thr Leu Lys
            20                  25                  30

Lys Leu Gly Tyr Asn Ala Ser Thr Asp Thr Lys Glu Leu Lys Thr Met
        35                  40                  45

Thr Pro Asp Val Tyr Ser Lys Ile Met Asn Val Ala Asn Asp Ser Ser
    50                  55                  60

Leu Gln Leu Tyr Ser Ser Ala Lys Ile Gln Lys Leu Gly Asp Lys Ser
65                  70                  75                  80

Pro Leu Glu Val Lys Ile Glu Thr Pro Glu Asn Ile Thr Lys Val Thr
                85                  90                  95

Gln Asp Met Tyr Arg Asn Ala Ala Val Thr Leu Gly Met Glu His Ala
            100                 105                 110

Lys Ile Thr Val Ala Ala Pro Ile Pro Val Thr Gly Glu Ser Ala Leu
        115                 120                 125

Ala Gly Ile Tyr Tyr Ser Leu Glu Ala Asn Gly Ala Lys Val Pro Gln
    130                 135                 140

Ala Asn Lys Asp Leu Ala Gln Glu Glu Leu Lys Ala Leu Ser Asp Ile
145                 150                 155                 160

Asn Ala Glu Asn Lys Asp Lys Ser Gly Tyr Asp Ala Asn Lys Leu Asn
                165                 170                 175

Val Ala Leu Ala Asp Ile Lys Ser Gly Leu Ala Lys Ala Lys Glu Ser
            180                 185                 190

Lys Gly Asn Leu Thr Glu Glu Asp Ile Arg Lys Ile Val Glu Asp Thr
        195                 200                 205

-continued

```
Leu Lys Asn Tyr Lys Leu Asp Gln Val Ile Thr Gly Asn Gln Ile Asn
    210                 215                 220

Ile Ile Ile Asn Phe Ala Leu Asn Leu Ser Lys Ser Asp Ile Leu Ser
225                 230                 235                 240

Asn Ala Asp Phe Thr Lys Thr Leu Asn Asp Leu Lys Gln Ser Ile Val
                245                 250                 255

Ser Gln Ala Gly Asp Ser Phe Lys Asn Ile Asn Leu Asn Phe Asp Ala
            260                 265                 270

Asp Lys Ala Leu Glu Asp Gly
        275
```